United States Patent
Montagner

(10) Patent No.: US 9,695,215 B2
(45) Date of Patent: Jul. 4, 2017

(54) METHOD FOR PRODUCING FIBROIN POWDER FROM SILK PRODUCTS OR FILAMENTS

(75) Inventor: Dino Montagner, S. Dona' di Piave (IT)

(73) Assignee: AL.PRE.TEC. SRL ALLERGY PREVENTION TECHNOLOGY ITALIA, Verona (IT)

( * ) Notice: Subject to any disclaimer, the term of this patent is extended or adjusted under 35 U.S.C. 154(b) by 0 days.

(21) Appl. No.: 14/410,472

(22) PCT Filed: Jun. 26, 2012

(86) PCT No.: PCT/IB2012/001274
§ 371 (c)(1),
(2), (4) Date: Dec. 22, 2014

(87) PCT Pub. No.: WO2014/001831
PCT Pub. Date: Jan. 3, 2014

(65) Prior Publication Data
US 2015/0337008 A1    Nov. 26, 2015

(51) Int. Cl.
*C07K 1/36* (2006.01)
*C07K 14/435* (2006.01)
*C08L 89/04* (2006.01)

(52) U.S. Cl.
CPC .......... *C07K 1/36* (2013.01); *C07K 14/43586* (2013.01); *C08L 89/04* (2013.01)

(58) Field of Classification Search
None
See application file for complete search history.

(56) References Cited

U.S. PATENT DOCUMENTS

| 4,233,211 A | * | 11/1980 | Ohtomo | A61K 8/64 424/69 |
| 4,297,400 A | * | 10/1981 | Kern | D06M 13/41 252/8.63 |
| 5,853,764 A | | 12/1998 | Tsubouchi | |
| 6,175,053 B1 | * | 1/2001 | Tsubouchi | A61L 15/32 602/41 |
| 2005/0081304 A1 | * | 4/2005 | Montagner | A41D 13/1263 8/115.51 |

FOREIGN PATENT DOCUMENTS

| EP | 0011161 A1 | 5/1980 |
| EP | 1116743 A1 | 7/2001 |
| WO | WO2010097651 | * 9/2010 |

OTHER PUBLICATIONS

Pubchem entry for Sodium carbonate (retrieved from http://pubchem.ncbi.nlm.nih.gov/compound/sodium_carbonate#section=Top on Nov. 18, 2015, 51 pages).*
Maat et al (from: Subjectification: various paths to subjectivity, Jan. 1, 2006, p. 298).*
Definition of seal (retrieved from http://dictionary.reference.com/browse/seal on Nov. 18, 2015, 9 pages).*
Definition of border (retrieved from http://dictionary.reference.com/browse/border on Nov. 18, 2015, 6 pages).*
International Search Report for corresponding International Application No. PCT/IB2012/001274, dated May 27, 2013.

* cited by examiner

*Primary Examiner* — Karlheinz R Skowronek
*Assistant Examiner* — Ronald Niebauer
(74) *Attorney, Agent, or Firm* — Egbert Law Offices, PLLC

(57) ABSTRACT

Method for producing a fibroin powder from silk products or filaments without sericin and dyes having the following phases: a) introduction of products or filaments into a very tightly-woven sealed bag with high filtering capacity to allow the treatment liquid but not the silk fibrils to exit; b) introduction of the bag into a tank with fresh and hot water with a mixer, in which soda is added to the water for a time of some hours; c) a rinsing phase of which the last is made with acetic acid in such a way as to make the fiber acceptable to the cutis as originally; d) phase of centrifugation and drying tumbler; e) tumbling phase, first opening the bags to throw away the material dried in the tumblers by pulverizing the fiber with a homogenous fragmentation in such a way as to keep the fibrils whole.

2 Claims, 1 Drawing Sheet

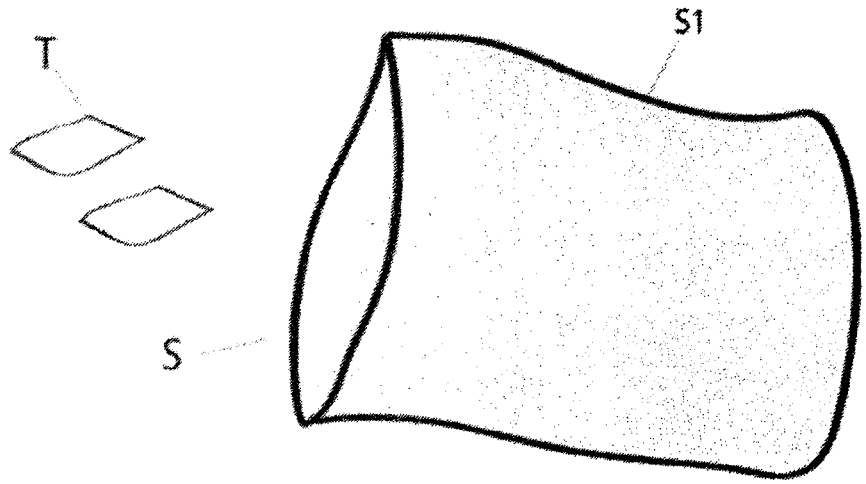

a) introduction of silk products or filaments into at least one very tightly-woven bag with high filtering capacity such as to allow the treatment liquid provided in phase b) to enter but not to allow the silk fibre to exit; said bag being bordered in such a way as to be sealed along the perimeter in correspondence of the seams;

b) introduction of at least said very tightly-woven bag into a tank of fresh and hot water with a mixer, wherein some soda is added to said water for a time of some hours;

c) execution of a rinsing phase of which the last is made with acetic acid in such a way as to make the fibre acceptable to the cutis as originally;

d) phase of centrifugation and drying tumbler;

e) tumbling phase, first opening the bags to throw away the material dried in the tumblers by pulverizing the fibre and grinding it with a homogeneous fragmentation in such a way as to keep the fibrils whole

METHOD FOR PRODUCING FIBROIN POWDER FROM SILK PRODUCTS OR FILAMENTS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a method for obtaining powder fibroin, starting for example from waste or scraps, as residues of the processing of silk products, said powder to be later used on its own or in a combined way also with agents, in the treatment of diseases of the human body, such as skin diseases and irritations, both internal and external to the human body, in re-epithelisation, such as the healing from sutures, in pharmacosmetics for moisturizing and anti-aging treatment, as well as a reconstructive means of tissues, and finally being used also as substrate, to facilitate the growth of stem cells.

2. Description of Related Art Including Information Disclosed Under 37 CFR 1.97 and 37 CFR 1.98

Silk is a protein material produced by different species of arthropods, among which there is traditionally the Bombix Mori, conventionally defined as silkworm. The wide use of the fibre is addressed to the textile field, but during the last decade it has found space in the biomedical sector as well. It is possible to reasonably state that silk, before being a textile fibre is a biomaterial, made up of two protein molecules, fibroin and sericin. Natural silk, in the form of a filament, consists of two continuous flosses of fibroin, which is a high molecular weight structural protein insoluble in water that constitutes about its 80%, wound and held together by a coating of sericin, a non-structural protein, belonging to a family of hydrophilic proteins that constitutes its remaining part. In the biomedical field it is known that the use of silk can occur only after the removal of sericin, a protein that gives origin to hypersensitivity and immunogenicity effects caused by the silk fibre as such. The removal of sericin from silk occurs by means of the degumming process. In this way one obtains fibres made up of the aggregation of fibroin molecules, linked to each other by a thick network of intermolecular hydrogen bonds.

In literature it is stated that silk fibroin, the main protein obtained from the cocoon secreted by Bombix Mori, thanks to its qualities of biocompatibility, oxygen and water vapour permeability and biodegradability is considered an excellent biomaterial. It is, in fact, widely used in the form of chemically regenerated fibre to obtain a wide range of structures, such as films, membranes, hydrogels and sponges, successfully used for the adhesion and the growth of different kinds of cells, and in its form of native fibre to obtain suture threads, spun fibres for the engineering of the anterior cruciate ligament and non-woven nets for the culture of osteoblasts, fibroblasts, hepatocytes and keratinocytes.

For example, a particular use of native fibres of silk fibroin has been carried out by the firm Sanitars s.p.a of Fiero (Brescia) that in IT 1 387182 describes a non-woven fabric, through the spunlace technology based on native fibres of silk fibroin intended for the use for the production of innovative gauzes and bandages for the treatment of skin pathologies, for the study and the design of prostheses implantable in surgery and for the production of supports in pure fibroin in the sector of tissue engineering.

In research there are various techniques of extraction of fibroin powder from silk, and in particular, China has proven to be one of the main Countries expert and practical in the sector. However, it must be said that the use of fibroin powder in said Country apparently finds application in the food sector as a supplement, its excellent properties having been recognized. Short research, not in depth, has also allowed to find some documents having various degrees of importance and that in the following are synthetically reported.

JP2010024196 describes a preparation method, suitable to obtain silk fibroin powder with the properties concerning the silk crystal structure preserved in it, and to improve yield in its tenacity decrease treatment. The preparation method of the silk fibroin powder includes a feeding process of the raw silk material in an aqueous solution of a neutral salt and the heating of the latter in such a way as to cause the raw material, silk, to swell. The following process requires the tenacity decrease treatment using alkalis or an acid in the aqueous solution of a neutral salt, then a phase that provides a process for neutralizing the aqueous solution of a neutral salt with the addition of an acid or an alkali, a phase for removing the weakened silk before dehydrating, a phase of washing of the raw silk extracted from the material, a phase of dehydration of the washed silk, a phase of drying of the dehydrated silk and a phase of crushing of the silk material.

JP2009292743 is a method for the production of silk fibroin powders soluble in water that has good solubility, in such a way as to be preserved for a long period, and adjusted on a solution with a high concentration of silk fibroin. Said method includes a process of dissolution of the raw silk material to obtain a silk fibroin solution, a process of filtration of the silk fibroin solution through an ultrafiltration membrane to remove the insoluble components, a process of desalination of the silk fibroin solution, and a process of drying and pulverization of the silk fibroin solution.

CN1456177 is a process with equipment for the natural production of a silk powder extract. After the sericin is extracted from natural silk, the residual extract of the natural silk is loaded in a closed container through its opening. The opening is then closed by a cover with a membrane. A pressure is released inside said container of about (2.5-3 MPa) for example introducing vapour for 6-15 minutes until the membrane breaks, freeing the powder.

JP2004315682 describes a method for producing a silk fibroin powder from silkworm, usable as a macromolecular material, insoluble in water, suitable to be treated and prepared for a cosmetic, food, a drug and a medical material. The powder is obtained from silk in a stable way without deterioration with high-efficiency to be used in an effective way and widen the application of silk from wild silkworm and indoor silkworm. The silk fibroin of the wild silkworm is dissolved with the addition of a solution containing copper such as ethylenediamine copper, ammonia, copper oxide and an alkaline solution of glycerol copper at 20-80 C, and an inorganic acid such as sulphuric acid, nitric acid and hydrochloric acid, or a fatty acid such as acetic acid, citric acid and acid tartaric is added to the silk solution dissolved allowing the crystal of proteins to precipitate. The precipitate of the end of the crystal is washed with water and dried with the aim of providing silk powder proteins.

JP2005281332 is another method for the production of white powder silk fibroin, which does not require desalination and without residues like salts and alkalis. The method for the production of powder silk fibroin comprises fibroin impregnating agents collected from silk proteins preferably with an aqueous alkaline solution, exposing the fibrous part of fibroin to superheated steam at 100-150° C. The method for the production of powder silk fibroin needs to bring the compound of fibrous fibroin collected from silk proteins in contact with an aqueous solution of hydrogen peroxide in a pressurized environment at 100-150° C., and then remove hydrogen peroxide from fibroin, dry and pulverize powder fibroin.

KR20020096638 the aim is to provide a high molecular weight silk peptide that can be added to food, insoluble in water. The method for the production of a high molecular weight silk peptide, insoluble in water fibroin powder comprises the phases of: hydrolysis of silk with calcium hydroxide or barium hydroxide, filtering of the hydrolysed silk, washing the filtered solid and drying it, making the alkali components precipitate in the filtered solution and subsequent filtering of the filtered solution to remove the alkali components, then removal of the concentration and drying of the filtered solution, in which the alkali components are made precipitate using at least one compound selected from sulphuric acid, oxalic acid, liquid carbon dioxide, dry ice and ammonium bicarbonate with the hydrolysis of silk taking place from 90° to 100° C. from 8 to 48 hours.

KR20010060437 describes a method for the production of silk powder, fibroin for use as a cosmetic material, an additive for cosmetics and other industrial uses. The raw silk material coming from cocoons, raw silk, waste cocoons, raw silk waste, silk waste and bourette fabric, degummed, is treated with an aqueous solution containing a neutral detergent. The material is then heated to over 150° C. and mixed in glycerol, ethylene glycol, or an aqueous solution of the latter to obtain a suspension, and then cooled. Water or alcohol like solvent methanol, ethanol and isopropyl alcohol is added to the suspension and stirred. The suspension is filtered and dried for the production of fibroin silk powder.

JP2001054359 proposes a method for obtaining high-quality high-efficiency fibroin silk powder in a shorter time than that required for the conventional process. After being sieved, the silk fibre is dissolved in a solution of water and alcohol including natural salt, such as sodium chloride. This solution is diluted and then fibroin is precipitated. The precipitated fibroin is separated while the neutral residual salt is removed from fibroin by washing. Finally, the washed fibroin is dried at about 30-50° C., and when sufficiently dry it is finely triturated.

JP11104228 is a production process consisting of the refining of silk fibres, to then dissolve the fibres in a refined solution of an acid or neutral salt. The low molecular weight materials are removed proceeding by dialysis. When the silk fibres are dissolved by means of the acid, the solution is neutralized with alkalis. The crystalline form of the fibroin is then pulverized.

U.S. Pat. No. 5,853,764 deals with a process for the preparation of crystalline powder of silk fibroin from a silk substance. The process for the preparation of fine powder of silk fibroin is such that the silk is put into an aqueous alkaline solution at a temperature of 95° C. or higher in order to cause a deterioration thereof, the resulting silk substance is subsequently subjected to the treatment with alkalis and the dry silk substance is pulverized into fine powder.

EP0875523 describes a method for the production of ultrafine powders of silk fibroin consisting of: a first step for the pulverization of the silk fibroin into a crushed powder status by means of mechanical means, a second phase for the pulverization of the silk fibroin powder crushed into a fine powder status by means of dry mechanical pulverization, a third phase for the pulverization of the fine silk fibroin powder into an ultrafine powder with an average diameter of particles of less than 10 μm by means of mechanical pulverization means and a following phase for treating the silk fibroin beta-powder in at least one of said first phases or after the three phases.

JP7278472 proposes an ultrafine silk fibroin powder that is produced by a process that includes the first step of crushing silk into a rough powder with a dry mechanical means, the second step of pulverizing the rough powder into a fine powder with a dry mechanical means and the third step of further pulverization of the fine powder into an ultrafine powder of maximum 10 mum of average size of the particles with a dry mechanical means, and wherein the silk fibroin powder is treated to have a beta-structure in at least one of the steps or afterwards. The obtained powder is fused with a resin, such as a solvent based on resin or a water-based resin and can contain aromatics.

JP7188563 provides to pulverize the rough silk fibroin powder with dry mechanical pulverization means, the second step of pulverizing to transform the rough silk fibroin powder into fine powder by pulverizing with mechanical means and a third phase to transform the fine silk fibroin powder into superfine powder of about <=10 μm of average diameter of the particles. The coating liquid containing the resulting very fine silk fibroin powder is applied on a substrate to provide a synthetic skin.

JP6339924 to produce an ultrafine silk fibroin powder there is provided a silk fibroin grinding process by a mechanical dry grinding means to obtain a rough powder (about 100 mum), a grinding process of the rough silk fibroin powder by a mechanical dry grinding means, such as a ball mill to obtain a very fine powder (about 20 mum) and a grinding process of the fine silk fibroin powder with a dry mill provided with mechanical grinding means to obtain an ultrafine powder (about 10 mum). In the grinding process, the transformation treatment applies methanol.

JP1313530 describes how to obtain a silk fibroin powder that can be insolubilized in a gel moulded biomaterial. It provides the addition of an alcohol to the system before or after the treatment in the execution of the freeze-drying of a solution of silk fibroin. A solution of silk fibroin is prepared, and an alcohol is added to it before or after freeze-drying.

JP58046097 deals with a method for obtaining filament-shaped silk powder fibroin useful as a base of cosmetics, pharmaceutical additives. Powder silk fibroin is prepared by soaking the silk thread (for example, cocoon, waste, raw silk, raw silk waste, silk thread, silk fabrics, etc.) into water contained in an autoclave, then one heats the yarns in the autoclave under pressure proceeding to the drying and the pulverization of the treated yarns. As an alternative method, the silk yarn thermally treated with the above-mentioned procedure is further treated in a high-pressure autoclave with saturated steam or superheated steam, and instantly released from a low-pressure environment to obtain expanded silk yarn, that is dried and pulverized obtaining fibroin silk powder.

U.S. Pat. No. 4,233,212 a process for the production of a fine powder of high purity silk fibroin in non-fibrous material shaped as particles requires the dissolution of the degummed silk compound with the addition of at least one solvent selected from the group consisting of an aqueous cupriethylendiamine solution, an aqueous solution of ammoniacal copper hydroxide, an alkaline aqueous solution of copper hydroxide and glycerol, an aqueous solution of lithium bromide, an aqueous solution of nitrate chloride, or calcium thiocyanate, magnesium and zinc, and an aqueous solution of sodium thiocyanate. Then some coagulant salt is added to the solution of silk fibroin with a silk fibroin concentration from 3 to 20% in weight, making the silk fibroin coagulate and, as it coagulates, precipitate, providing to the dehydration and drying of the so formed gel.

These and other solutions that have not been described yet offer a very wide range of silk processing methods to obtain powder fibroin from silk and in principle they are surely valuable. It is therefore reasonable to consider as known:

The recovery of silk waste, already degummed, in order to carry out a processing to obtain fine powder of silk fibroin;

The processing of silk waste to obtain silk fibroin powder, which comprises at least one or more steps in which one carries out a dry grinding phase by means of mechanical means;

Always a processing cycle, if necessary with the aid of heating functions, in which to the grinding phase a phase is added, which requires a solution of liquids, afterwards said compound to be filtered and then dried or dehydrated;

The solution of liquids used also along with the pulverization or grinding phase can comprise compounds based on alcohol, chlorides, alkalis or acids;

The silk fibroin powder is used as a preparation for a cosmetic, food, a drug and a material for sanitary use also in the form of a gel.

Drawbacks

According to the applicant the above-described solutions can still be considered insufficient, as, in relation to the preset objectives, supposedly not able to offer in the first place some considerable quantities of fibroin powder of a size greater than a micron in order to allow the start in a reasonable way of an industrial process. In other words, the systems used until today seem to be rather empiric, still in the embryonic stage, and insufficient, being substantially chemical processes, from the point of view of the protection of and of the attention to the health of the public of reference. This with particular reference to the processes, as occurs in most cases, that use solutions of liquids based on alcohol, chlorides, alkalis or acids to facilitate the dissolution of fibroin in microparticles. In particular in the known processes the so obtained fibroin is of sub-micron sizes, and as a consequence it is water-soluble. In literature, because of the sizes, it can be considered as a product with a high mutagenic risk if used in the pharmacological field.

Another drawback is linked to the fact that the single fibroin powder is not at all sufficient to inhibit bacterial proliferation when it is used for pharmacological purposes. In particular, following laboratory checks, according to some studies, it has been discovered that it is not particularly effective in the reduction of bacterial proliferation. For example, a laboratory test that includes the following conditions has been carried out:

micro-organism *Staphylococcus aureus* ATCC 6538

Inoculum: bacterial suspension, $1 \times 10^5$ UFC/mL diluted in nutrient broth and saline in a ratio of 1/12. 0.5 mL of the suspension are put in contact with 200 mg of powder to obtain a homogenous mixture.

At the end of the contact time, the obtained suspensions were extracted with 50 ml of Neutralizing agent and then filtered to move away the sample Contact time: 1 and 8 hours at 37° C.

Neutralizing agent: 30 g/l azolecithin, 30 g/l Tween 80, 5 g/l sodium thiosulphate, 1 g/l L-histidine, 0.68 g/l KH2P04 (pH at 7.210.2)

Sterilization of the sample: no

In this case it can be noted that when fibroin powder only is used, with the aim of reducing bacterial proliferation, the percentage of reduction equals 0 both in the case with a Contact time of 1 h and with a Contact time of 8 h.

All this considered, it is evident that it is necessary to find some alternative solutions with reference to the production method and more effective in relation to the characteristics of the obtained semi-finished product with respect to those available until now or anyway inferable with respect to the above-described solutions.

Therefore, the aim of the present invention is to offer on the market a method of production of fibroin powder in such a way as to provide a component particularly suitable for the sector of the products for medical, pharmacological, cosmetic, cosmoceutical use and as a biomaterial.

BRIEF SUMMARY OF THE INVENTION

This and other aims are achieved by the present invention according to the characteristics as in the enclosed claims, solving the above-mentioned problems, by a method for producing a fibroin powder from silk products or filaments without sericin and dyes, and that comprises at least the following phases:

a) introduction of products or filaments into at least one very tightly-woven bag with high filtering capacity such as to allow the treatment liquid provided in phase b) to enter but not to allow the silk fibrils to exit; said bag being bordered in such a way as to be sealed along the perimeter in correspondence of the seams;

b) introduction of at least said very tightly-woven bag into a tank, with fresh and hot water with a mixer, in which some soda is added to said water for a time of some hours;

c) execution of a rinsing phase of which the last is made with acetic acid in such a way as to make the fibre acceptable to the cutis as originally;

d) phase of centrifugation and drying tumbler;

e) tumbling phase, first opening the bags to throw away the material dried in the tumblers by pulverizing the fibre and grinding it with a homogenous fragmentation in such a way as to keep the fibrils whole.

With the obtained fibroin powder then one can also obtain a non-woven fabric for example by electrospinning.

Advantages

In this way, by the considerable creative contribution the effect of which constitutes immediate technical progress, some aims are achieved. In the first place the described production method allows to obtain a considerable amount of fibroin powder, subsequently usable for other processing and applications.

The silk product and filament, from which the described method starts, can be treated in advance with or without antimicrobial of the Aegis type. If it is without antimicrobial, this powder under different forms can be applied to accelerate life, bacterial proliferation, up to about 50 times/hour with respect to a normal buffer. Whereas with the antimicrobial the result of bacterial reduction calculated on the 8 h is of about 99% as from the enclosed test.

| | Sample *Staphylococcus aureus* ATCC 6538 | | |
|---|---|---|---|
| | UFC/ml inoculum $T_0$ | UFC/ml inoculum 1 h | % reduction 1 h |
| Reference cellulose fluff | $1.0 \times 10^5$ | $1.0 \times 10^5$ | |
| Fibroin Powder | $1.0 \times 10^5$ | $5.6 \times 10^6$ | 0 |
| | | $5.4 \times 10^6$ | 0 |
| Dermasilk Powder | $1.0 \times 10^5$ | $9.0 \times 10^3$ | 91.0 |
| | | $8.4 \times 10^3$ | 91.6 |

| | Sample *Staphylococcus aureus* ATCC 6538 | | |
|---|---|---|---|
| | UFC/ml inoculum $T_0$ | UFC/ml inoculum 8 h | % reduction 8 h |
| Reference cellulose fluff | $1.0 \times 10^5$ | $7.1 \times 10^5$ | |
| Fibroin Powder | $1.0 \times 10^5$ | $11.5 \times 10^6$ | 0 |
| | | $12.3 \times 10^6$ | 0 |
| Dermasilk Powder | $1.0 \times 10^5$ | $1.5 \times 10^3$ | 98.5 |
| | | $7.5 \times 10^2$ | 99.3 |

In the case in which products or filaments of the type treated with antimicrobial are used, the so obtained silk fibroin powder has particular advantages. In more detail, besides constituting an excellent barrier to skin irritations and to grazes because it actively protects the damaged horny layer, controls the development of bacteria (in particular of staphilococcus aureus), substantially reducing the possibility of infections. As a whole, therefore, it is possible to state that this material is particularly suitable for the treatment and the prevention of various skin-mucosal disorders and affections, among which for example, dermatitises, inflammations and infections, sores, ulcers, wounds, etc., helping the regeneration of cutis and mucosae, in some cases there being provided the use also as a skin topical treatment, but also, for example, added on a substrate in non-woven plaster or on its own (e.g. by electrospinning) or still in the form of a slow release capsule, obviously taking into account the amino acid chain.

With respect to the pre-existing solutions, it is important the fact that in the cases in which one uses enzymatic extraction processes, which are most of the cases, one manages to break the protein chain, while in the solution proposed by the applicant with the object of the present invention, one can obtain a product that keeps the protein chain whole in the form of a fibril. Furthermore, it is necessary to point out the filtering function of the particular bag used in the described production method, which in this case has a filtering capacity of the pores of about 5.9 μm used in the described phases (a) and (b) of the applicant's processing method. In more detail, the known techniques do not seem effective, due to the fact that the fibroin powder, being water-soluble, is substantially dispersed during the conventional filtration phase, which precedes the collection, whereas in the solution suggested by the applicant, thanks to the particular filtering bag, the loss of the material is limited in a measure between 10% and 20%, to be extracted from the bag only in a weakened fibre condition.

These and other advantages will appear from the following detailed description of at least one preferred solution with the aid of the schematic drawings enclosed whose details are not to be considered limitative but only illustrative.

BRIEF DESCRIPTION OF THE DRAWINGS

FIG. 1 is a flowchart of the method for producing fibroin powder from silk products or filaments.

DETAILED DESCRIPTION OF THE INVENTION

The present invention relates to a method for producing fibroin powder using silk products or filaments. The fibroin powder, as already observed previously, above all if of the type obtained from products or filaments of silk treated with antimicrobial, is particularly suitable in the treatment of mainly skin and mucosal affections of the human body, and as a support in the regeneration of tissues. The phases that follow each other for the execution of the mentioned process require at first the availability of silk products or filaments.

In this case, where the silk products or filaments are the result of a previous processing of silk products in a case it is preferable that the same products were made with some silk that was treated with some antimicrobial agent based on quaternary ammonium or equivalent. In other words, it is supposed that the silk with which said products are obtained was first degummed.

In this case, where the treatment of the silk fabric with antimicrobial is provided, a liquid bath is prepared, with a temperature of about 25° C., inside which the antimicrobial solution has been added. Said solution consists of an antimicrobial agent, for example based on quaternary ammonium, and in more detail of the type identified in the product ÆGIS Dow Corning 5700 (3-trimethoxysilylpropyldimethyloctadecyl ammonium chloride) marketed by ÆGIS Environmental Management, Inc., preliminarily dissolved in a percentage of water with the addition of SILANE (of the family of silicone softeners) as a binder. The percentage of participation in the solution of the antimicrobial agent ÆGIS is in proportions included between about 5%-15% for 1 kilogram of dry fabric or article to be treated. Therefore, 30/35 kg of solution per 1 kg of fabric to be treated are generally needed. Approximately, the silk fabric, once soaked, is kept in movement, and the liquid environment in which it is soaked with pH 5, is taken to a temperature first of 30° until reaching 50° C. with pH 8, for a total period of about 45'/60'.

Once said silk fabric has been treated with said agent having an antimicrobial function, one proceeds to a centrifugation cycle of the so treated fabric or article. From the following processing of the so treated fabric or article some products or filaments of fabric (T) are left, which are treated with the above-described antimicrobial agent.

The method of the present invention requires the availability of products or filaments of silk fabric (T) without sericin and dyes, in such a way as to prearrange a processing cycle that requires at least the following phases:
  a) introduction of the products or filaments of silk fabric for example in square pieces of about 20 cm per side, into at least one very tightly-woven bag (S) of the size of about 50 cm×80 cm, for example of the type in polyester (or another synthetic material, such as polyamide) produced by the company PFG Inc. USA, called Pristine, whose fabric has an air porosity capacity in the air comprised in a range between 20-33 L/dm$^2$/min., whose pores have a size of about 5-6 μm; said bag that contains the silk waste and scraps is of the bordered type, with respect to the stitches sealed (S1), for example, with the same material as the bag, in such a way as to obtain a soft casing, and once filled and closed with a rim (S1) in correspondence of the closure, introduced into a tank for example of the beater type, with a mixer;

b) the treatment liquid has been previously introduced into said tank, preferably some dyeworks fresh water, brought to the temperature in the tank of about 96-97° C. and to which powder soda is added in the preferred measure of 4 g/L. The stay time in the tank of said bags (S) is comprised in a range between 6 h-10 h; in this way, by combining temperature, pH and stay time, the silk of the products or filaments is weakened in such a way that the fibrils are detached remaining whole and insoluble;

c) a cycle for rinsing the bags (S) is carried out, which preferably comprises 6/7 phases, in cold or lukewarm water, whose first 5 phases for example with pure water and the last, for example, two phases with acetic acid in order to bring the silk pH from a value of about 10.5 back to a pH of 5.5÷6;

d) the bags (S), which contain the weakened fabrics of the so treated silk products or filaments, are subjected first to a centrifugation phase and then in a relaxed drying machine of the Tumbler type, also at 80° C. for about 2/3 h;

e) once the drying has been carried out, one proceeds to the opening of each bag (S), throwing the material into machines suitable to carry out the tumbling for example a jar mill, in order to pulverize it, or to grind it, until obtaining a silk fibroin powder for about 2/3 hours in such a way as to have a fine homogenous fragmentation, up to about 10/30 μm keeping the fibrils whole.

With the so obtained fibroin powder then it is also possible to obtain a non-woven fabric for instance by an electrospinning process, or to be used in addition to supports, of various nature, suitable for the pharmaceutics, cosmetic, or cosmoceutical industry. Furthermore, it is observed that in the case of the so obtained fibroin powder treated with antimicrobial agent, laboratory tests have identified the particular inhibitory function of pathogens in the development and in the treatment of *Candida* infection. The result has been obtained by preparing a solution with a ratio of about 1 mcg (fibroin powder treated with antimicrobial agent)/1 L of product. In the same amount it is particularly suitable for disinfecting floors and surfaces in general, as also as an additional component to conventional detergents for washing-machines for disinfecting clothes during washing. In a further preferred embodiment the previously described developed process as in phases (a-e), can consider the treatment of silk products or filaments also not treated with antimicrobial, as already described, and consequently, first provide to the obtainment of the fibroin powder without antimicrobial, and then carry out a phase of application of said antimicrobial based on quaternary ammonium, by means of bath, sprinkling, nebulisation or other techniques. According to another preferred embodiment, the previously described developed processes in phases (a-e) can consider the treatment of wool products or yarns, rather than of silk, both of the type preliminarily treated with antimicrobial and without, in the latter case said antimicrobial agent is applied once said powder has been obtained.

The invention claimed is:

1. A method of producing silk fibroin powder from silk products or silk filaments in which the silk products or silk filaments do not have sericin and and have not been subjected to a dyeing treatment, the method comprising:
    introducing the silk products or filaments into at least one woven bag having a border and sealed along stitches thereof, the bag having pores having a diameter of between 5 and 10 micrometers;
    closing the bag along the border;
    introducing a treatment liquid having quaternary ammonium into a tank, the tank having a mixer therein;
    heating the treatment liquid to a temperature of 96° C. and 97° C.;
    introducing the bag into the tank;
    maintaining the bag in the tank for a period of between 6 hours and 10 hours such that the silk from the silk products or silk filaments is weakened so that fibrils are detached from a remainder of the silk products or silk filaments, the fibrils being insoluble;
    rinsing the silk in phases having water in which at least one phase includes acetic acid so as to bring a pH of the silk to a pH of between 5.5 and 6;
    centrifuging the bag containing the weakened silk products or silk filaments;
    drying the bag in a tumbler drying machine;
    opening the bag and transferring the silk into a tumbler; and
    pulverizing the silk so as to obtain a homogenous fragmentation and to keep the fibrils whole so as to produce a fibroin powder having a final particle size of between 10 micrometers and 30 micrometers.

2. The method of claim 1, the bag being formed of a polyester material.

* * * * *